US012699943B2

(12) United States Patent
Donhowe et al.

(10) Patent No.: US 12,699,943 B2
(45) Date of Patent: Aug. 4, 2026

(54) DETECTING EVENTS DURING A SURGERY

(71) Applicant: c/o Verily Health Inc., Dallas, TX (US)

(72) Inventors: Caitlin Donhowe, Mountain View, CA (US); Joëlle Barral, Mountain View, CA (US); Zhi Yuan Foo, Mountain View, CA (US); Niranjan Sridhar, San Mateo, CA (US)

(73) Assignee: Verily Life Science LLC, Dallas, TX (US)

( * ) Notice: Subject to any disclaimer, the term of this patent is extended or adjusted under 35 U.S.C. 154(b) by 1205 days.

(21) Appl. No.: 17/452,270

(22) Filed: Oct. 26, 2021

(65) Prior Publication Data

US 2022/0129822 A1    Apr. 28, 2022

Related U.S. Application Data

(60) Provisional application No. 63/198,561, filed on Oct. 27, 2020.

(51) Int. Cl.
| | |
|---|---|
| *G09B 23/28* | (2006.01) |
| *A61B 34/20* | (2016.01) |
| *A61B 34/30* | (2016.01) |
| *G06N 20/00* | (2019.01) |
| *G06Q 10/0639* | (2023.01) |
| *G06V 20/40* | (2022.01) |

(52) U.S. Cl.
CPC ....... *G06Q 10/06398* (2013.01); *A61B 34/20* (2016.02); *A61B 34/30* (2016.02); *G06N 20/00* (2019.01); *G06V 20/46* (2022.01);

*G09B 23/28* (2013.01); *A61B 2034/2065* (2016.02); *G06V 2201/10* (2022.01)

(58) Field of Classification Search
CPC ..................................................... G09B 23/28
See application file for complete search history.

(56) References Cited

U.S. PATENT DOCUMENTS

| | | | |
|---|---|---|---|
| 6,754,380 B1 * | 6/2004 | Suzuki .................. | G06T 7/0012 |
| | | | 382/156 |
| 11,574,403 B2 * | 2/2023 | Ngo Dinh .............. | G06N 3/045 |

(Continued)

OTHER PUBLICATIONS

International Application No. PCT/US2021/072033, International Search Report and Written Opinion, mailed Jan. 31, 2022, 9 pages.

(Continued)

*Primary Examiner* — Kurt Fernstrom
(74) *Attorney, Agent, or Firm* — Kilpatrick Townsend & Stockton LLP

(57) ABSTRACT

One example method for detecting events during a surgery includes receiving surgical video of a surgery comprising a plurality of video frames; identifying, by a first trained machine-learning ("ML") model, an event during a surgical procedure based on the surgical video; determining, by the first trained ML model, a subset of the plurality of video frames, the subset of the plurality of video frames corresponding to the event; determining, by a second trained ML model, a characteristic of the event based on the subset of the plurality of video frames; and generating metadata corresponding to event based on the characteristic of the event.

24 Claims, 7 Drawing Sheets

(56)        References Cited

U.S. PATENT DOCUMENTS

| | | | |
|---|---|---|---|
| 11,625,834 B2 * | 4/2023 | Xu | G06T 7/277 |
| | | | 382/103 |
| 2009/0088634 A1 * | 4/2009 | Zhao | A61B 1/00193 |
| | | | 600/425 |
| 2011/0020779 A1 * | 1/2011 | Hannaford | G09B 23/28 |
| | | | 715/702 |
| 2016/0314710 A1 * | 10/2016 | Jarc | G09B 23/285 |
| 2018/0357514 A1 * | 12/2018 | Zisimopoulos | G06V 10/764 |
| 2019/0325574 A1 * | 10/2019 | Jin | G06V 10/454 |
| 2020/0265273 A1 * | 8/2020 | Wei | G06N 3/048 |
| 2020/0273581 A1 | 8/2020 | Wolf et al. | |

OTHER PUBLICATIONS

Khalid et al., "Evaluation of deep learning models for identifying surgical actions and measuring performance", JAMA network open 3.3 (2020): e201664-e201664.

\* cited by examiner

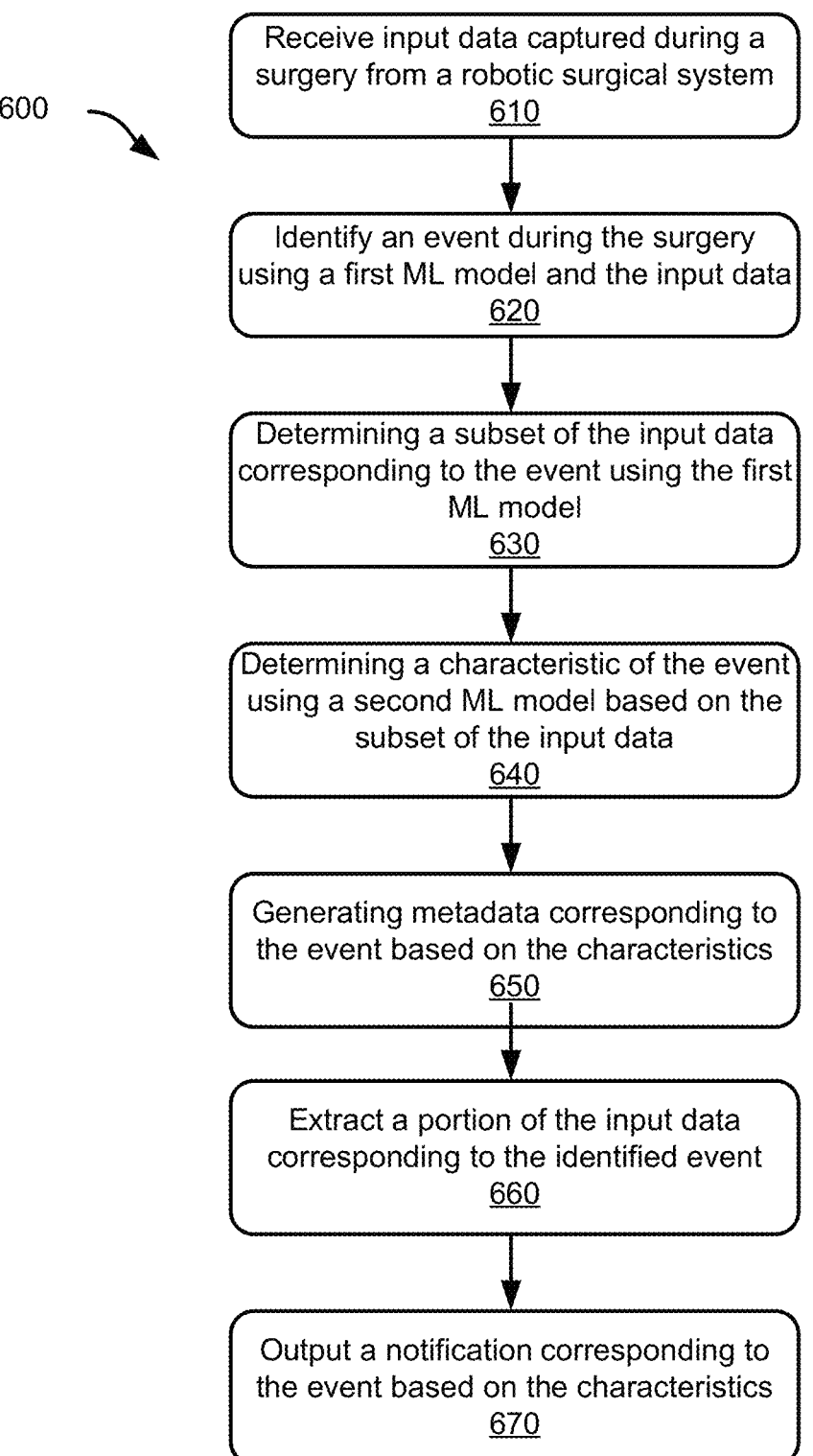

600

Receive input data captured during a
surgery from a robotic surgical system
610

Identify an event during the surgery
using a first ML model and the input data
620

Determining a subset of the input data
corresponding to the event using the first
ML model
630

Determining a characteristic of the event
using a second ML model based on the
subset of the input data
640

Generating metadata corresponding to
the event based on the characteristics
650

Extract a portion of the input data
corresponding to the identified event
660

Output a notification corresponding to
the event based on the characteristics
670

*FIG. 6*

DETECTING EVENTS DURING A SURGERY

CROSS-REFERENCE TO RELATED APPLICATIONS

This application claims priority to U.S. Provisional Patent Application No. 63/198,561, filed Oct. 27, 2020, titled "Detecting Events During A Surgery," the entirety of which is hereby incorporated by reference.

FIELD

The present application generally relates to robotic surgery and more particularly relates to detecting events during a surgery.

BACKGROUND

As robotic surgeries become more and more popular, a large volume of surgical videos is being recorded every day, especially for laparoscopic surgeries. These videos contain valuable information and can be important resources for tasks such as surgery analysis and new surgeon training However, videos can run for multiple hours and are unlikely to be reviewed again in their entirety more than once or twice. Thus, valuable information regarding the surgical procedure may be recorded during the surgery but not appreciated unless the video is reviewed in its entirety.

SUMMARY

Various examples are described for detecting events during a surgery. One example method for detecting events during a surgery includes receiving surgical video of a surgery comprising a plurality of video frames; identifying, by a first trained machine-learning ("ML") model, an event during a surgical procedure based on the surgical video; determining, by the first trained ML model, a subset of the plurality of video frames, the subset of the plurality of video frames corresponding to the event; determining, by a second trained ML model, a characteristic of the event based on the subset of the plurality of video frames; and generating metadata corresponding to event based on the characteristic of the event.

One example system includes a non-transitory computer-readable medium comprising a first trained machine-learning ("ML") model and a second trained ML model; a processor communicatively coupled to the non-transitory computer-readable medium and configured to execute processor executable instructions stored in the non-transitory computer-readable medium to: receive surgical video of a surgery comprising a plurality of video frames; identify, using the first trained machine-learning ("ML") model, an event during a surgical procedure based on the surgical video; determine, using the first trained ML model, a subset of the plurality of video frames, the subset of the plurality of video frames corresponding to the event; determine, using the second trained ML model, a characteristic of the event based on the subset of the plurality of video frames; and generate metadata corresponding to event based on the characteristic of the event.

One example non-transitory computer-readable medium includes processor-executable instructions configured to cause a processor to receive surgical video of a surgery comprising a plurality of video frames; identify, using the first trained machine-learning ("ML") model, an event during a surgical procedure based on the surgical video; determine, using the first trained ML model, a subset of the plurality of video frames, the subset of the plurality of video frames corresponding to the event; determine, using the second trained ML model, a characteristic of the event based on the subset of the plurality of video frames; and generate metadata corresponding to event based on the characteristic of the event.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 6 shows an example method for detecting events during a surgery; and

DETAILED DESCRIPTION

Figure 1:
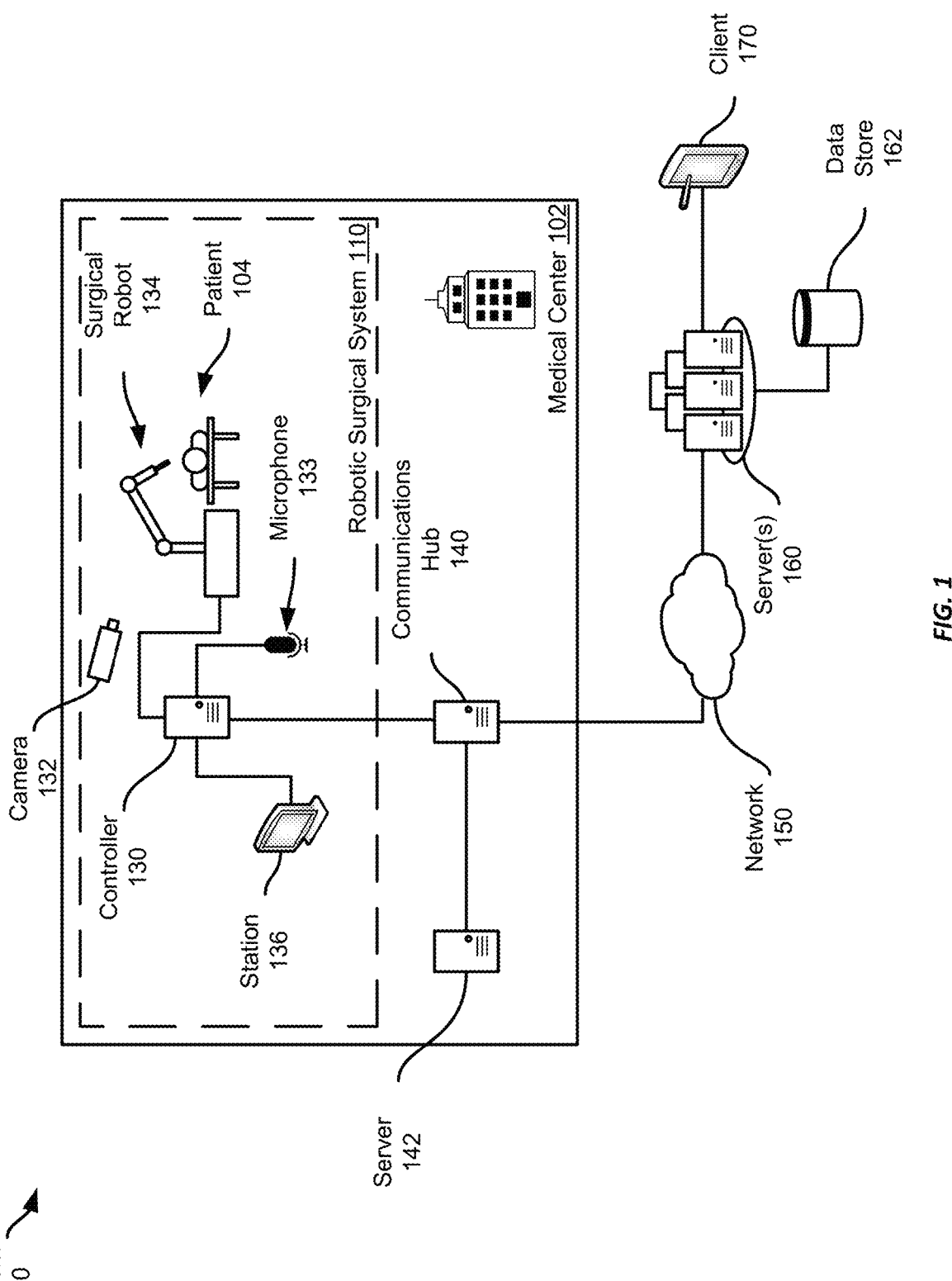
FIGS. 1-3 show example systems for detecting events during a surgery.

Examples are described herein in the context of detecting events during a surgery. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

During a robotic surgery, a surgeon controls a surgical robot to perform certain tasks. To perform different aspects of the surgery, the surgeon manipulates controls on the surgical robot that then causes robotic arms or tools connected to the surgical robot to move or perform operations, such as cutting, grasping, ablating tissue, etc. Typically, these surgeries are minimally invasive, and so the surgeon is only able to view and perform the surgery based on video provided by an endoscope inserted into the patient. This video is also recorded so that it may be reviewed after the surgery by the surgeon or other medical professionals. In addition, the surgical robot logs other information, including movements performed by the surgical robot, tool use, tools that are connected or disconnected, etc. Further, some operating rooms ("ORs") may have cameras or microphones to record the surgery being performed externally to the patient, in addition to (or instead of) the internal endoscopic video.

The video, audio, and robotic data gathered during the surgery can be used by a surgery analysis system according to this disclosure to detect events during the surgery and further analyze those events to identify particular characteristics of interest. This event and characteristic information can then be used to generate metadata, which may be output as notifications, annotations to the surgical video, etc.

For example, during a robotic surgery, a surgeon may dissect tissue within the surgical site. The endoscope captures video of the dissection, including tool movement, orientation, and pose. In addition, the robotic surgical system records detailed kinematic data as the dissection is performed (as well as throughout the surgery). The video and kinematic data can then be analyzed by a machine-learning ("ML") model to detect events during surgery, such as the dissection. For example, the ML model in this example has been trained to recognize certain events over a series of video frames and to recognize certain actions taken based on kinematic data. By processing the video and kinematic data, it can identify learned events that occur during the course of the surgery. It can then identify video segments (or segments of kinematic data) corresponding to the identified events. Thus, after this ML model operates on the surgical video and kinematic data, it may identify multiple different events that have occurred during the surgery. Alternatively, multiple different ML models, each trained to recognize one or more different events, may separately analyze the video and kinematic data to identify the various events. The collection of identified events may then be used to identify the portions of video or kinematic data corresponding to those events. In addition, the ML model generates metadata that identifies the type of event, e.g., dissection, ablation, etc. and associates the metadata with the corresponding portions of the video or kinematic data (or both).

The video or kinematic data may then be processed by one or more additional ML models that have been trained to determine characteristics of discrete, identified events, depending on the type of events that have been identified. For example, an ML model may be trained to assess the quality of a suturing technique used to close an incision. The ML model then receives segments of video or kinematic data (or both) corresponding to a suturing event detected in the surgical video and outputs an assessment, such as a score or multiple scores for different aspects of the suturing technique. Similarly, another ML model may be trained to detect adverse events or severities of adverse events, such as undesirable or unanticipated bleeds, unintentional cuts or punctures, etc. The ML model can then assess the type and severity of the adverse event and generate metadata with the assessment information. Still other types of trained ML models can be executed on different segments of video, audio, kinematic data, etc. to provide more detailed characteristics of the various events detected by the event detection ML model.

The generated metadata from the various ML models includes information identifying the corresponding segment of data, e.g., the starting and ending frames of video corresponding to an event, the type of the event, and characteristics of the event, such as scores, severities, errors, etc. The metadata can then be used to annotate the corresponding data, such as by inserting bookmarks into the video and corresponding comments. This example system then also extracts segments of video (or other data) corresponding to the detected events and associates the appropriate metadata with the extracted segment so that it may be viewed discretely without the need to review the full video (or other data). In addition to annotating the video or other data, the example system may also generate additional notifications, such as by notifying an attending surgeon that, based on poor scores for surgical techniques, a surgeon should receive additional training on one or more of those techniques. Alternatively, if the surgical video includes multiple examples of a highly scored surgical technique, a notification may be generated that identifies the video as a candidate training video to be shared with incoming surgery residents or other medical professionals. Further, in examples where the system operates in real-time during the surgery, it may output notifications to an attending surgeon that the surgeon performing the surgery is having difficulties or has made mistakes that may require correction or may warrant the attending surgeon taking over the surgery. Still other types of notifications may be generated depending on the detected events and characteristics of those events.

Examples according to this disclosure may provide a robust way to exhaustively analyze data generated during a surgery, including identifying any and all events of interest and characteristics of those events. This information can then be used to annotate surgical video (or other data) and provide other indications to medical professionals or administrative staff about any potential performance issues (or exemplary performance) by its surgeons. In examples where the system runs in real-time, it can further provide in-surgery feedback to the surgeon or other members of the surgery team that may help address issues occurring during the surgery or identify anatomical anomalies that may warrant modifications to the course of the surgery.

This illustrative example is given to introduce the reader to the general subject matter discussed herein and the disclosure is not limited to this example. The following sections describe various additional non-limiting examples and examples of detecting events during a surgery.

Referring now to FIG. 1, FIG. 1 shows an example system 100 for detecting events during a surgery. The example system 100 includes a robotic surgical system 110 located at a medical center 102 that is in communication with one or more remote servers 160 via a communications network 150, such as the Internet. The remote server(s) 160 have an associated data store 162 that may include one or more databases or other servers. A user may use client 170 to access the server(s) 160, such as to create or edit surgeries to be performed, to obtain surgical plan information, to review videos obtained during a robotic surgical procedure, etc.

The robotic surgical system 110 includes a controller 130, a surgical robot 134, and a station 136 usable by personnel in the OR, such as to view surgery information, video, etc., from the surgical robot 134, which may be used to operate on a patient 104 (though the patient is not part of the robotic surgical system 110). The controller 130 is in communication with a server (or servers) 142 at the medical center 102 that may be involved in detecting events during a surgery as well as a communications hub 140.

The communications hub 140 enables, optimizes, or improves communication to the server(s) 142 within the medical center 102 or to remote server(s) 160 via the network 150. In addition, the communications hub 140 provides access to patient or other medical information stored locally at the medical center 102. Further, in some examples the communications hub 140 may operate as a remote server 160, such as in an example in which the communications hub 140 is not local to the medical center 102.

The surgical robot 134 is any suitable robotic system that can be used to perform surgical procedures on a patient, to provide simulations of surgical procedures, or to provide training functionality to allow a surgeon to learn how to control a surgical robot 134, e.g., using exercises to train particular movements or general dexterity, precision, etc. It should be appreciated that discussions throughout this detailed description related to surgical procedures are equally applicable to simulated procedures or training exercises using a surgical robot 134.

A surgical robot 134 may have one or more articulating arms connected to a base. The arms may be manipulated by a controller 130, which may include one or more user interface devices, such as joysticks, knobs, handles, or other rotatable or translatable devices to effect movement of one or more of the articulating arms, as well as one or more display devices to display information to the surgeon during surgery, e.g., video from an endoscope, information from patient medical records, previously obtained images (e.g., X-rays, MRI images, etc.). The articulating arms may be equipped with one or more surgical instruments to perform aspects of a surgical procedure. Different surgical robots 134 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

In some examples, surgical robots (or a respective controller, e.g., controller 130) may be configured to record data during a surgical procedure. For example, the surgical robot 134 may record inputs made by the user, actions taken by the surgical robot 134, times (e.g., timestamps) associated with each input or action, video from one or more cameras of the surgical robot, etc. In some examples, surgical robot may include one or more sensors that can provide sensor signals, such as thermocouples, pulse sensors, SvO2 or SpO2 sensors, one or more cameras, etc., or other information to be recorded, such as temperatures, pulse information, images, video, etc. Such information may be obtained by the sensor and transmitted to a computing device within the surgical robot 134 itself, to the controller 130 for storage, or to any suitable computing device, e.g., server 140 or server(s) 160. Furthermore, while only one surgical robot 134 is depicted, any suitable number of surgical robots may be employed within a surgical robotic system 100.

The controller 130 in this example includes a computing device in communication with the surgical robot 134 and is able to control access and use of the robot. For example, the controller 130 may require that a user authenticate herself before allowing access to or control of the surgical robot 134. As mentioned above, the controller 130 may include, or have connected to it, one or more user input devices capable of providing input to the controller, such as a keyboard, mouse, or touchscreen, capable of controlling the surgical robot 134, such as one or more joysticks, knobs, handles, dials, pedals, etc.

In addition to the surgical robot 134, information captured by one or more OR cameras 132 or microphones 133 may be transmitted to the controller 130 or other computing device, e.g., the communications hub 140, the medical center server(s) 142, or to the remote servers 160. This information may be analyzed, in addition to (or instead of) video captured by one or more cameras manipulated by the surgical robot 145, by one or more trained ML models to detect events during the surgery or to determine characteristics of those events.

To begin a surgery, a user may log into the controller 130, and the controller 130 may then activate the surgical robot 134, provide access to the surgical robot 134 to the surgery team, and provide access to patient information, including copies of one or more EHR records, patient images (e.g., x-rays, ultrasounds, etc.), etc.

As discussed above, the robotic surgical system 110 includes a communications hub 140 that includes a computer or server that manages communications with the controller 130 and surgical robot 134 within the medical center 102 and provides communications out of the medical center 102 and to the network 150. For example, the communications hub 140 may include a networking device, such as a router or a switch. However, the communications hub 140 may include one or more server devices that provide additional features, such as user access to patient or other medical records received from the server(s) 160, etc., while also providing secure access to locally stored medical records to the controller 130 or surgical robot 134. In some examples, the communications hub 140 is an optional component that may be omitted, or may be a virtual machine running on an underlying computing system.

It should be appreciated that while this example shows only one surgical robot 134 and controller 130 in communication with the communications hub 140, in some examples, the communications hub 140 may be in communication with multiple controllers 130 and surgical robots 134. For example, the medical center 102 may have one communications hub 140 per floor, or one for every four surgical robot 134/controller 130 combination, etc. In some examples, the medical center 102 may only have a single communications hub 140 that is in communication with all controllers 130 and surgical robots 134 at the medical center 102.

As discussed above, the robotic surgical system 110 is in communication with one or more remote servers 160 via network 150. The network 150 may be any combination of local area networks ("LAN"), wide area networks ("WAN"), e.g., the internet, etc. that enable electronic communications between the communications hub 140 and the remote servers 160.

The remote server(s) 160, in conjunction with the data store 162, store records about one or more surgeries to be performed, previously performed surgeries, videos from previously performed surgeries, surgical plans, etc. The remote server(s) 160 may also provide functionality to enable a user to create new surgeries, schedule the surgeries, access surgical plans including resources needed for a scheduled surgery, assign medical personnel, assign a patient, allocate an OR and a robotic surgical system for the surgery, and review videos obtained during prior surgeries to prepare for an upcoming surgery or evaluate the performance of the previously performed surgery, etc. Thus, the server(s) 160 provides management and administrative control over the creation of new surgeries and the access to the data underlying those surgeries. It also provides a web portal that a user may access via a client 170 to create new surgeries, manage previously created surgeries, and access information regarding upcoming or previously performed surgeries, such as surgical plans, videos and corresponding metadata, etc.

During surgery, the surgical robot 134 captures video via one or more surgical tools, such as an endoscope, and transmits the video to the controller 130. The controller 130 outputs the video to one or more displays, such as a display at the controller 130 or another location, such as station 136. The captured video may then be processed in real-time or near-real-time using one or more trained machine-learning ("ML") techniques to detect events during the surgery. In some examples, the controller 130 may instead stream the video to a remote computing device instead to process the video in real-time or near-real-time, e.g., the controller 130 may stream the video to the communications hub 140, server(s) 142, or to a remote computing device, e.g., remote server(s) 160, for processing. Alternatively, processing may not be done in real-time (or near-real-time), but may instead be performed after the surgery is completed.

Figure 2:
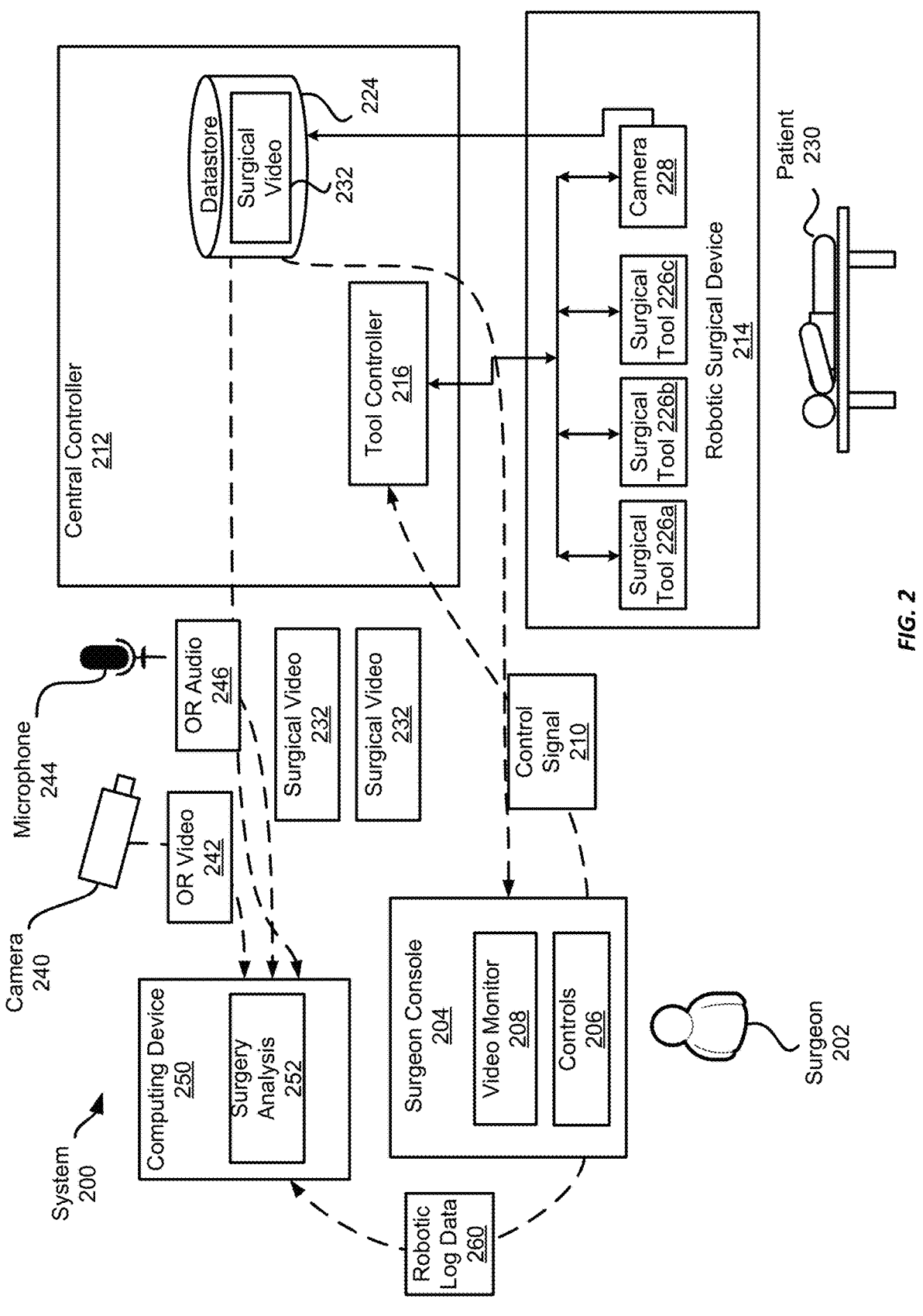

Referring now to FIG. 2, FIG. 2 shows an example system 200 for detecting events during a surgery. This example system 200 includes a robotic surgical device 214 configured to operate on a patient 230, and a central controller 212 to control the robotic surgical device 214. The system 200 also includes a surgeon console 204 connected to the central controller 212 and the robotic surgical device 214. The surgeon console 204 is operated by a surgeon 202 to control and monitor the surgeries performed using the robotic surgical device 214. In addition to these components, the system 200 might include additional stations (not shown in FIG. 2) that can be used by other personnel in the operating room, for example, to view surgery information, video, etc., sent from the robotic surgical device 214. In this example, the robotic surgical device 214, the central controller 212, the surgeon console 204 and other stations are connected directly to each other, though in some examples they may be connected using a network, such as a local-area network ("LAN"), a wide-area network ("WAN"), or any other networking topology known in the art that connects the various stations in the system 200.

The robotic surgical device 214 can be any suitable robotic system utilized to perform surgical procedures on a patient. For example, the robotic surgical device 214 may have one or more robotic arms connected to a base. The robotic arms may be manipulated by a tool controller 216, which may include one or more user interface devices, such as joysticks, knobs, handles, or other rotatable or translatable devices to effect movement of one or more of the robotic arms. The robotic arms may be equipped with one or more surgical tools to perform aspects of a surgical procedure, and different surgical tools may be exchanged during the course of the surgical procedure. For example, the robotic arms may be equipped with surgical tools 226A-226C. Each of the surgical tools can be controlled by the surgeon 202 through the surgeon console 204 and the tool controller 216.

In addition, the robotic surgical device 214 is equipped with one or more cameras 228, such as an endoscope, configured to provide a view of the operating site to guide the surgeon 202 during the surgery. In some examples, the camera 228 can be attached to one of the robotic arms of the robotic surgical device 214 controlled by the tool controller 216 as shown in FIG. 2. In other examples, the camera 228 can be attached to a mechanical structure of the robotic surgical device 214 that is separate from the robotic arms (which may have any number of tools interchangeably attached to them) such as a dedicated arm for carrying the camera 228.

Different robotic surgical devices 214 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses.

As a result, different types of surgical robots, including those without robotic arms, such as for endoscopy procedures, may be employed according to different examples. It should be understood that while only one robotic surgical device 214 is depicted, any suitable number of robotic surgical devices may be employed within a system 200.

In some examples, robotic surgical devices (or a respective controller) may be configured to record data during a surgical procedure. For example, images and videos of the surgical procedures performed by the robotic surgical device 214 can also be recorded and stored for later use. For instance, a storage server 224 can be employed by the robotic surgical device 214 to store surgical videos 232 of surgical procedures captured by the camera 228.

In the example shown in FIG. 2, surgical video 232 of a robotic surgical procedure captured by the camera 228 can also be transmitted to the surgeon console 204 and be displayed on a video monitor 208 in real time so that the surgeon 202 can view the procedure while the surgical tools 226 are being used to operate on the patient 230. In this example, the surgeon 202 uses the surgeon console 204 to control the surgical tools 226 and the camera 228, and uses controls 206 on the surgeon console 204 to maneuver the surgical tools 226 and camera 228 by sending corresponding control signals 110 to the tool controller 216.

In addition to the camera 228 of the robotic surgical device 214, the system 200 also includes one or more cameras 240 positioned within the OR, such as on a wall, the surgeon console 204, or any other suitable location. The camera(s) 240 may be positioned to capture fields of view including the robotic surgical system, the area surrounding the patient, or other locations within the OR. OR video captured by the camera(s) 240 are sent to a computing device 250 that includes surgery analysis software 252. As can be seen in FIG. 2, this computing device 250 also receives surgical video from any cameras 228 installed on the robotic surgical device 214 as well. And while the surgical video 232 is sent directly to the computing device 250 in this example, in some examples, the surgical video 232 may be relayed to the computing device 250 from the surgeon console 204, either in real-time, periodically during the surgical procedure, or after the surgical procedure has concluded.

In addition to the OR camera(s) 240, the OR may also be equipped with one or more microphones 244 that capture and transmit OR audio data 246 to the computing device 250. The microphone(s) 244 may be positioned at any suitable location within the OR or may be integrated into a component of the surgical robot, e.g., in the surgeon console 240.

The surgeon console 204 (or another aspect of the surgical robot) may provide robotic log data 260 to the computing device 250 for analysis, either in real-time or after the surgery has completed. In examples where the computing device 250 is integrated within the surgical robot, e.g., the surgeon console 204, the robotic log data 260 may be accessed from memory within the surgical robot. In other examples, however, the robotic log data may be transmitted by any suitable wired or wireless communications technique, such as Ethernet, Wi-Fi, Bluetooth, Firewire, Thunderbolt, universal serial bus ("USB"), etc.

As shown in FIG. 2, the computing device 250 includes surgery analysis software 252 to process the surgical video 232, OR video 242, OR audio 246, or robotic log data 260 captured during the surgical procedure. The surgery analysis software 252 analyzes the received data to recognize events occurring during the surgical procedure. As will be discussed in more detail below, the surgery analysis software 252 analyzes frames of the received video (e.g. surgical video 232 or video 242), the OR audio 246, and the robotic log data 260 to recognize these events. In this example, the surgery analysis software 252 employs ML models that have been trained on data corresponding to different events that may occur during a surgery, including incisions, dissections, resections, ablations, cauterizations, suturing, adverse events, etc., though in some examples, multiple different trained ML models to recognize different types of events.

The surgery analysis software 252 also includes ML models trained to analyze characteristics of specific types of events that may occur during a surgery. For example, the surgery analysis software 252 may include multiple different trained ML models to analyze characteristics of surgical techniques, such as suturing, dissection, resection, ablation, cautery, etc.; detecting surgical errors; detecting anomalous anatomy; detecting non-standard surgical techniques; etc. These different trained ML techniques may operate sequentially or in parallel (or a combination) to determine characteristics of different events detected in one or more of the surgical video 232, OR video 242, OR audio 246, or robotic log data 260.

Figure 3:
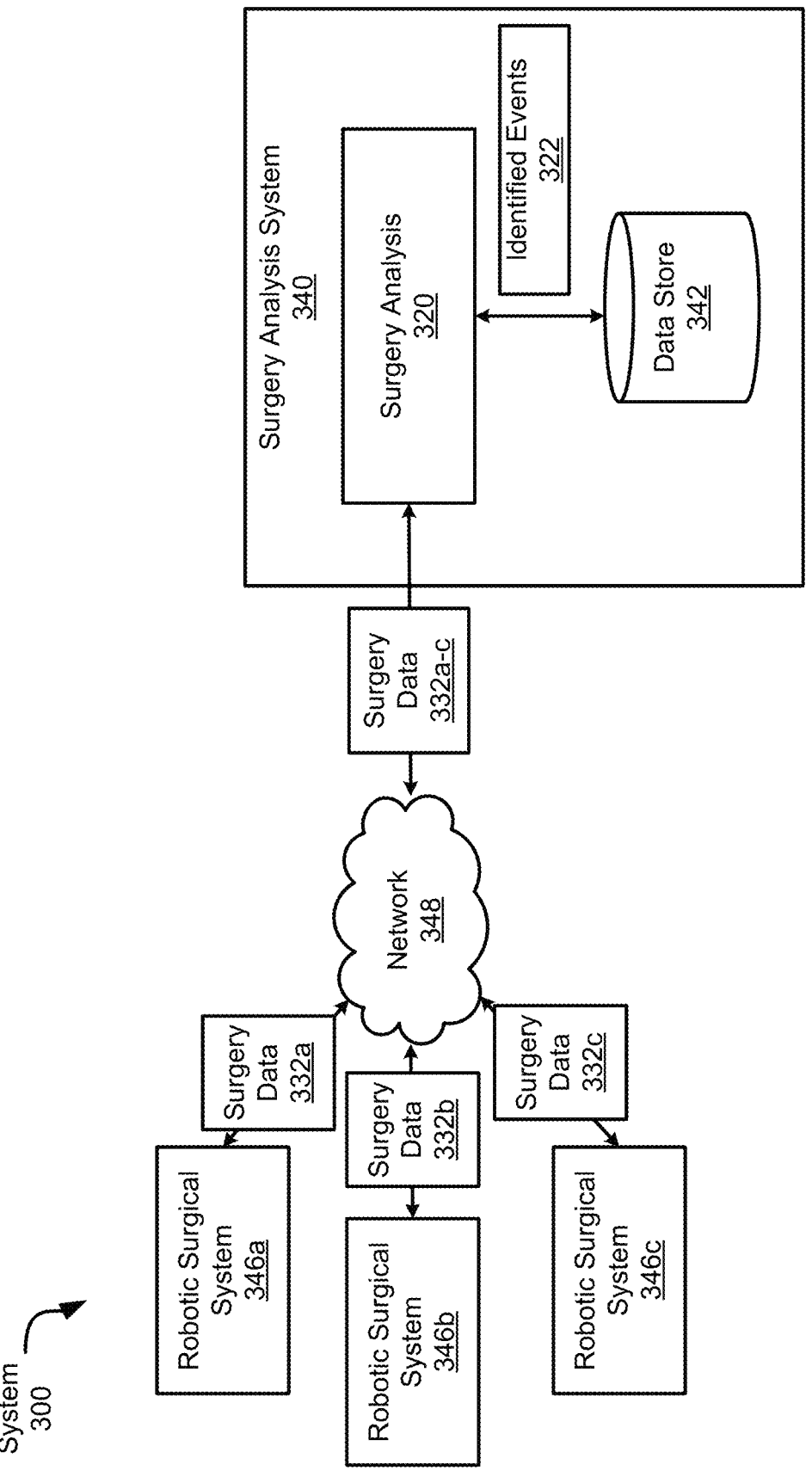

It should be appreciated that although FIG. 2 illustrates the presented technique of detecting events during robotic surgery in the context of a particular system 200, it can be implemented in other types of systems and settings. For example, this technique can be implemented in a computing device separate from a system 200 or can be performed offline after the surgical procedure is completed. FIG. 3 illustrates an example of a computing environment where a surgical video analysis system 300 is configured to detect events during a surgical procedure as described herein.

In the example system 300 shown in FIG. 3, the surgery analysis system 340 includes surgery analysis software 320 generally as described above with respect to FIG. 2. The surgery analysis software 320 is configured to detect events during robotic surgery and determine characteristics of those events.

In this example, the robotic surgical systems 346a-c are configured in a way similar to the robotic surgical system 200 as discussed above with respect to FIG. 2 except that the robotic surgical systems 346a-c do not include surgery analysis software 252. Instead, the robotic surgical systems 346a-c send captured surgery data 332a-c (e.g., video, audio, data logs, etc.) to the surgery analysis system 340 for analysis. In some examples, the surgery data 332a-c is sent through a network 348, such as a LAN, a WAN, or any other networking topology or technology known in the art that connects the robotic surgical systems 346a-c to the surgery analysis system 340.

The surgery analysis software 320 receives the surgical data 332a-c and detects events during a surgery generally as described above and in more detail below. In the example shown in FIG. 3, the identified events and corresponding characteristics 322 are recognized by the surgery analysis software 320, which stores the identified events and corresponding characteristics 322 in a data store 342 and associates them the corresponding surgical data, e.g., a surgical video. In addition, the surgery analysis software 320 may extract portions of the surgical data 332a-c, such as video segments or related audio or robotic log data, corresponding to an identified event and associate metadata generated based on the determined event and characteristics with the extracted portions. These extracts and corresponding metadata may then be stored in the data store 342 or made available to users of the system, e.g., to client devices 170, for review or other action. In some examples, the surgical analysis software 320 may output notifications, e.g., to indicate further training is needed, that the captured event is a high-quality or notable example of the particular event, the patient has unusual anatomical features, etc.

Figure 4:
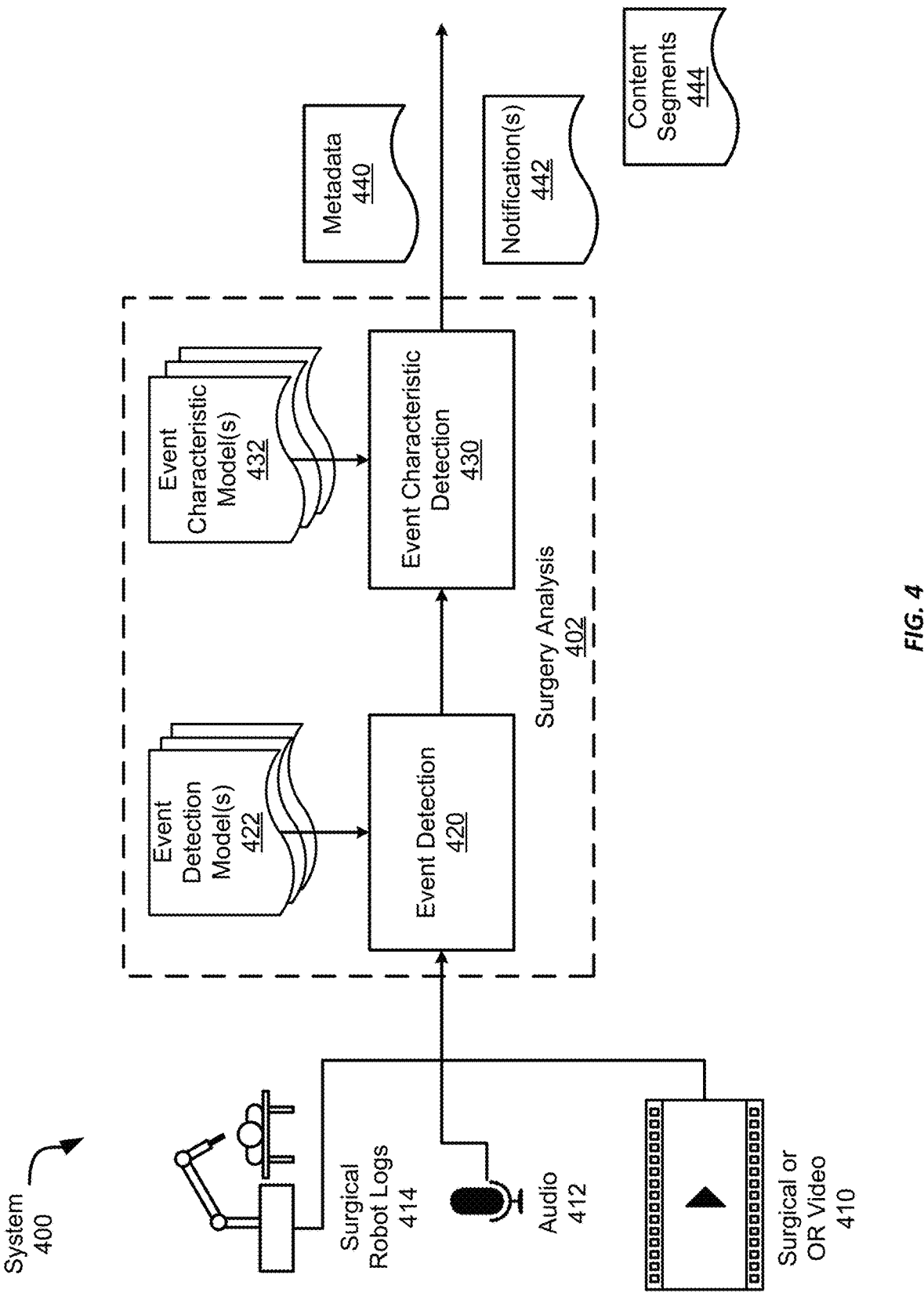
FIGS. 4-5 show example software architectures for detecting events during a surgery.

Referring now to FIG. 4, FIG. 4 shows a block diagram of system 400 for detecting events during a surgery that includes surgery analysis software 402. The surgery analysis software 402 receives different kinds of input data in this example, including surgical or OR video 410, audio 412, and surgical robot logs 414 in this example. The surgery analysis software 402 processes the incoming input data and generates and outputs one or more of metadata 440, notifications 442, or content segments 444.

As discussed above, data for use by the surgery analysis software 402 can come from a variety of sources, including video from one or more endoscopes, video from one or more cameras positioned within the OR, audio from one or more microphones within the OR, log data from a surgical robot (including kinematic data about robotic arms or tools, tool usage information, tool change information, etc.), electronic health records ("EHR"), other equipment in the OR, etc. Depending on the configuration of the system 400, input data from one or more of these different data sources may be used. For example, if the OR is not equipped with cameras and microphones, the input data may include only surgical video 401 from an endoscope and surgical robot logs 414. Or in some examples, surgical video alone 410 may be employed. Any suitable combination of different input data may be used according to different examples.

The surgery analysis software 402 receives the input data and employs event detection software 402 to detect events captured within the input data. Depending on the implementation of the system 400, the input data may be received and processed in real time as the data is generated. For example, surgical video 232 captured by an endoscope may be streamed to a surgeon console 204 as depicted in FIG. 2. In addition, that same video may be streamed to the surgery analysis software 402.

In this example, event detection software 420 employs one or more trained event detection ML models 422 to analyze the incoming input data to identify events that occurred during the surgery. Event detection software 420 in this example attempts to identify or classify occurrences within the input data that correspond to events used to train the event detection models 422. For example, an event detection model may be trained on surgical video to recognize different occurrences within a surgery, such as incising, suturing, ablating, cautery, resecting, etc. Further, event detection models may be trained to detect events within specific types of surgical procedures. For example, one event detection model may be trained to recognize different phases of a cholecystectomy, while another event detection model may be trained to recognize typical anatomical features encountered during a gastric bypass. Any number of such event detection models may be trained and employed by the event detection software. Further, which models are selected for use by the event detection software 420 or event characteristic detection software 430 may be based on the surgical procedure being performed.

A recognition model, e.g., trained event detection ML model(s) 422 or event characteristic model(s) 432, can be a machine-learning ("ML") model, such as a convolutional neural network ("CNN"), e.g. an inception neural network, a residual neural network ("Resnet") or NASNET provided by GOOGLE LLC from MOUNTAIN VIEW, CALIFORNIA, or a recurrent neural network, e.g. long short-term memory ("LSTM") models or gated recurrent units ("GRUs") models. The recognition model can also be any other suitable ML model may be trained to recognize resources depicted in one or more video frames, such as a three-dimensional CNN ("3DCNN"), a dynamic time warping ("DTW") technique, a hidden Markov model ("HMM"), etc., or combinations of one or more of such techniques— e.g., CNN-HMM or MCNN (Multi-Scale Convolutional Neural Network). In some examples, the ML models may employ adversarial training, e.g., generative adversarial networks, and may also employ autoencoders ("AEs") to facility training or recognition, e.g., AEGANs. The surgery analysis software 420 may employ the same type of recognition model or different types of recognition models for event detection or characteristic detection.

It should be appreciated that an "event" for purposes of the event detection software 420 is not limited to actions taken by a surgeon via the surgical robot using a surgical tool. Instead, an "event" is a recognized feature of the surgery as captured by the input data. Thus, "events" may include the surgical techniques discussed above (incising, suturing, etc.), but may include unrecognized or non-standard surgical techniques as well as other occurrences such as bleeding, changes in heart rate, fluid collection, surgical errors (e.g., unexpected incisions or incisions made in wrong locations or wrong tissue), etc. In addition, "events" may include abnormal features within the patient. Abnormal features may include tissues or organs with non-standard sizes or shapes, organs located in abnormal positions, missing or duplicate organs, atypical amounts of adipose tissue, unusual adhesions, etc. One or more ML models may be trained to identify such events (or other events) and identify where in the input data the event was recognized.

To identify where in the input data an event is recognized, the event detection software 420 employs one or more event detection models 422 to detect events within the input data. When an event detection model 422 detects an event, it generates information identifying the location of the event in the input data. For example, the event detection model may identify a beginning of the event, e.g., using a timestamp or frame number, and an end of the event, e.g., using a time stamp or frame number, or by identifying a duration of the event. The information may be output as a pair of values, e.g., (event_begin$_{frame}$, event_end$_{frame}$), or as a tuple of arbitrary size, e.g., (event_type, input_stream_id, event_begin, event_end, surgeon_id, date, time_begin, time_end), with any suitable information included. Still other data formats for identified events may be employed.

As discussed above, the input data may be provided to any number of trained event detection models 422. These models 422 may be run in parallel or in sequence, or a combination of the two. Further, the event detection models 422 may be executed on different computing devices, which may then return the output to the surgery analysis software 402. For example, the surgery analysis software may be executed by server 142 in FIG. 1, which may transmit the input data to a group of servers, e.g., servers 160, established as a cloud computing environment, where different trained event detection models 422 are executed on different individual servers. The results of executing the various models 422 may then be returned to the server 142. Such processing may happen in real time during a surgery, where input data may be streamed from the robotic surgical system 110 to the server 142, which may then stream the input data to the server(s) 160, which respond with information identifying detected events.

The event detection software 420 receives the output of the event detection model(s) 422. The event characteristic detection software 430 then executes one or more trained event characteristic ML models 432 based on the detected events. For example, the events may be identified in different ways, such as by a high-level category (surgical technique, adverse events, anatomy, etc.) or a lower-level type of event (e.g., suturing, cutting, ablating, etc.) The event characteristic models 432 process the input data and the identified events to determine one or more characteristics for each of the detected events. The characteristics may include information indicating an assessment of surgical skill, an determination of a rarity of an abnormal anatomical feature, a determination of a severity of an error or adverse event, a determination of a pulse rate of a detected pulse, detected audio in the OR (e.g., "oops" or "bleed"), etc. The event characteristic detection software 430 receives the output from the event characteristic model(s) 432 and generates outputs based on the events and characteristics.

Output from the surgery analysis software 402 may include metadata 440 that accompanies one or more of the input data streams, such as the surgical video. Events and corresponding characteristics may be determined to correspond to particular portions of the surgical video, e.g., based on time stamps in corresponding surgical robot logs or particular groups of frames within the surgical video. The surgery analysis software 402 may then generate metadata to accompany the surgical video. The metadata may be generated to identify a starting frame number, an ending frame number, an event type, and the identified characteristic(s) of the event.

The metadata may be incorporated into the same file as the surgical video or may be inserted into a metadata file associated with the surgical video. For example, the surgery analysis software 402 may generate one or more bookmarks within the surgical video and associate labels with the bookmarks, such as by naming the bookmark after the event and providing additional fields identifying the characteristic(s) of the event.

In some examples, the surgery analysis software 402 may generate one or more notifications 442 based on the detected events and corresponding characteristic(s). For example, if the surgery analysis software 402 detects an error made by a surgeon or poor surgical techniques, it may output a notification to an attending surgeon or a head of a surgery department identifying the errors or deficient surgical skill. Such a notification may be sent as a text message (e.g., short message service ("SMS") messages), an email, a page, an automated phone call, a message through a secure healthcare messaging application, etc. If the event is detected in real-time during the surgery, the notification may be output on a screen visible to a supervising surgeon, e.g., as a textual or graphical message or sent as a text message or page. The notification may include a text message, similar to the example discussed previously, or it may include a segment of surgical video corresponding to the detected error, adverse event, or poor surgical technique. Such an embodiment may allow the supervising surgeon to view the identified event and determine appropriate corrective action, if any. In some examples, the notification may be generation of an entry onto a feedback report for the surgeon, e.g., a weekly or monthly feedback report. In addition, the notification may identify potential corrective action. For example, if poor surgical technique is detected, one or more training exercises may be identified that correspond to the particular surgical technique and output in a message to the surgeon or to an attending or department head as suggested training for the surgical technique.

Further, in addition to (or instead of) the metadata or notifications, the surgery analysis software 402 may generate one or more content segments 444 based on the input data and the detected events and characteristics. For example, if an event is detected, a portion of the surgical video corresponding to the event may be extracted from the surgical video and stored as a separate video. The extracted video may have metadata associated with it, e.g., based on the event and characteristic(s), such as by naming the surgery video after the detected event or characteristic(s) of the event. Similarly, portions of audio or surgical robot logs can be extracted to correspond with detected events and metadata corresponding to such extracted portions can be included, e.g., in a filename or as embedded metadata.

In some examples, to include metadata, the surgery analysis software may generate an initial set of introductory video frames with information about the video clip, such as the date of the surgery, the name of the surgeon, the type of event, and one or more characteristics of the event. Such video frames may be generated to appear as static text for a fixed duration (e.g., 5 or 10 seconds) to introduce the video segment. Further, in examples where multiple streams of input data are received, segments of multiple data streams may be extracted corresponding to the same event and associated with each other and generated metadata. For example, each respective data stream extract may be saved as a discrete file and named using common information. Metadata may be embedded in one or more of the files or may be stored as a further discrete file and named according to the same common convention.

It should be appreciated that while the discussion of the system 400 has described certain functionality being implemented in software, in some aspects, the implementations may employ hardware, e.g., dedicated ASICs, neural networks, etc., to perform some or all of the functionality discussed above.

Figure 5:
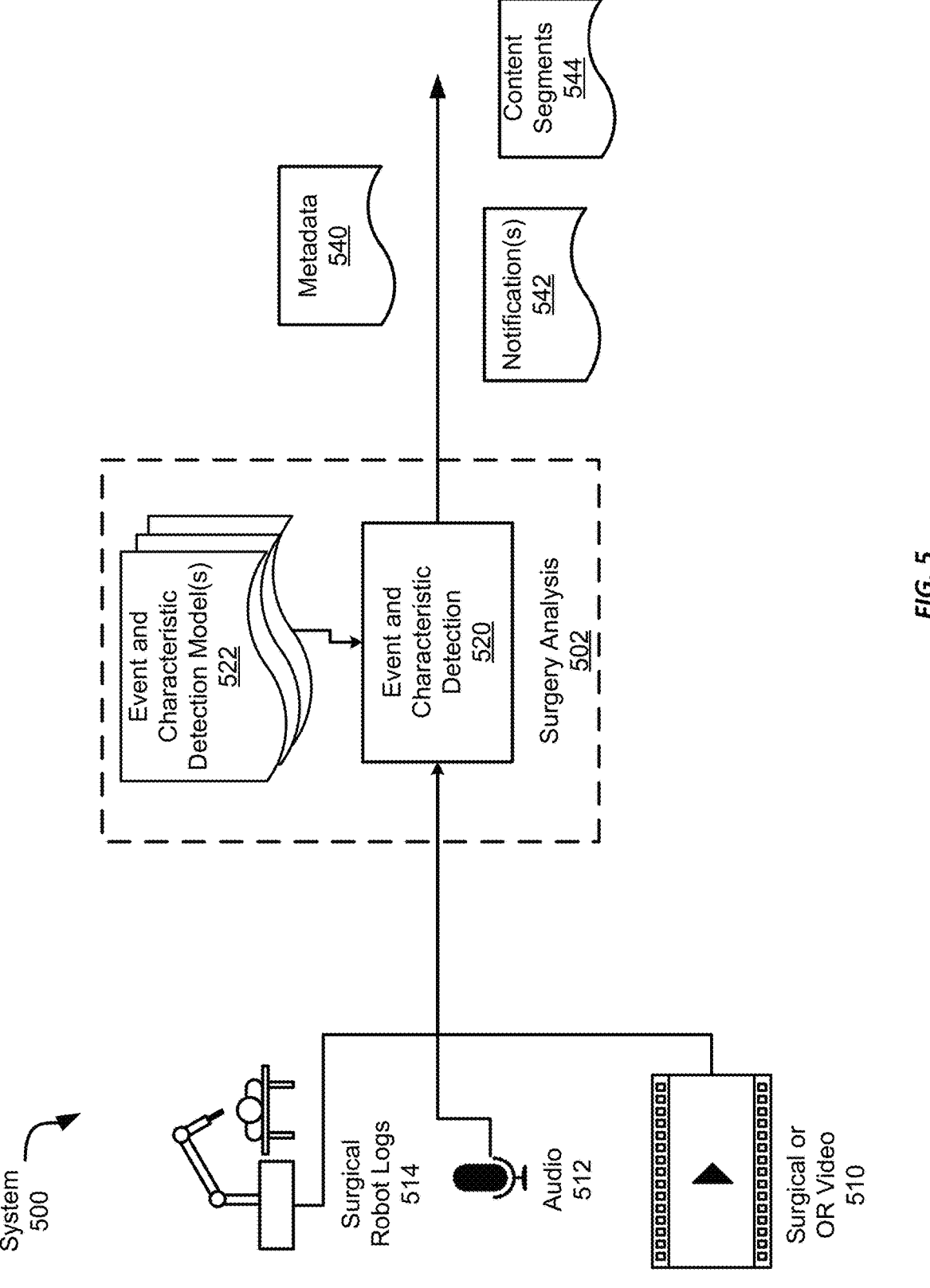

Referring now to FIG. 5, FIG. 5 shows a block diagram of system 500 for detecting events during a surgery that includes surgery analysis software 502. The surgery analysis software 502 receives different kinds of input data in this example, including surgical or OR video 510, audio 512, and surgical robot logs 514 in this example. The surgery analysis software 502 processes the incoming input data and generates and outputs one or more of metadata 540, notifications 542, or content segments 544.

The example system 500 shown in FIG. 5 is similar that shown in FIG. 4, except the surgery analysis software 502 combines the event detection and characteristic detection functionality into one software component 520 and the trained ML models 522 perform both event detection and characteristic detection. Thus, rather than using discrete models 422, 432 to detect events and then characteristics, the models 522 in FIG. 5 detect both. Though it should be appreciated that separate event detection and characteristic detection models, e.g., models 422, 432, may be used with the event and characteristic detection software 520 in FIG. 5.

Thus, the event and characteristic detection software 520 receives input data streams, such as surgical or OR video 510, audio 512, or surgical robot logs 514 and provides data to the event and characteristic detection model(s) 522 and receives one or more identified events and corresponding characteristics. This information is then used to generate one or more of metadata 540, notifications 542, or content segments 544 generally as described above with respect to FIG. 4. Further, as discussed above, if multiple event and characteristic detection models are employed, they may be executed in parallel, in series, or a combination of the two. In some examples, the models 522 may be implemented across multiple different computing devices, such as in a cloud computing environment as discussed above.

Referring now to FIG. 6, FIG. 6 shows an example method 600 for detecting events during a surgery. This example method will be discussed with respect to the example systems shown in FIGS. 1, 2, and 4. In particular, the method 600 will be discussed with respect to the surgery analysis software 402 of FIG. 4 executing on server 142 of the system 100 in FIG. 1. Further, the robotic surgical system 200 shown in FIG. 2 will be employed as detail for the robotic surgical system 110 shown in Figure. However, it should be appreciated that any suitable system according to this disclosure may be employed.

At block 610, the surgery analysis software 402 receives input data captured during a surgery from a robotic surgical system generally as discussed above with respect to FIG. 4. For example, the surgery analysis software 402 may receive surgical video of a surgery comprising a plurality of video frames. Such surgical video 232 may be received from an endoscope camera 228, though in some examples, surgical video 242 may be captured from one or more OR cameras 240 positioned within the OR, while audio 246 may be captured by one or more microphones 244 positioned within the OR. Robotic log data 260 may be received from the surgical robot, e.g., from the surgeon console 204. Still other input data may be received from other sources. For example, patient data may be obtained from an electronic health record ("EHR") system, patient imagery may be obtained from an imaging system, e.g., magnetic resonance imaging ("MRI"), ultrasound, X-ray, etc., patient vital signs may be captured from heart monitors or blood oxygen sensors. Other input data may be received from other equipment present in the OR, such as anesthesia machines, ventilators, etc.

At block 620, the event detection software 420 identifies an event during the surgery using a first trained ML model. In this example, the event detection software 420 provides at least a portion of the input data to one or more trained event detection models 422, which then detect events based on the input data, generally as discussed above with respect to FIG. 4. It should be appreciated that the event detection software 420 may determine any number of events within the input data.

At block 630, the event detection software 420 determines a subset of the input data corresponding to the event using the first trained ML model. In this example, when a trained event detection model 422 detects an event, it determines the corresponding portion of the input data for the event. For example, if the input data includes surgical video, the trained event detection model(s) 422 identify video frames corresponding to the identified event. In examples where the input data includes robotic log data 260, the event detection model 422 may identify a subpart of the log corresponding to the detected event. Similarly if other types of input data are received, e.g., audio data, information from patient health record (e.g., EHR), information from other equipment in the ER, the event detection model(s) 422 detect events in such data and identify a subpart of such input data corresponding to the event. The event detection software 420 receives the identified event and the identified subset of the input data corresponding to the event from the event detection model(s) 422 generally as discussed above with respect to FIG. 4. It should be appreciated that the event detection software 420 may determine a subset of the input data for each identified event within the input data.

At block 640, the surgery analysis software 402 determines, using a second trained ML model, a characteristic of the event based on the subset of the input data. In this example, the event characteristic detection software 430 provides the determined subset of the input data to the trained event characteristic model(s) 432, which determine one or more characteristics corresponding to the event. As discussed above, characteristics may be assessments of surgical skill, determinations of a rarity of an abnormal anatomical feature, determinations of a severity of an error or adverse event, determinations of a pulse rate of a detected pulse, etc. Further, events may have one or more characteristics associated with them. For example, an event may have both an assessment of surgical skill and a severity of an error.

At block 650, the surgery analysis software 402 generates metadata corresponding to the event based on the determined characteristics generally as discussed above with respect to FIG. 4.

At block 660, the surgery analysis software 402 extracts a portion of the input data corresponding to the identified event, generally as discussed above with respect to FIG. 4.

At block 670, the surgery analysis software 402 outputs a notification corresponding to the event based on the characteristic(s). For example, a notification may be generated indicating that an assessment of a surgical skill did not meet a threshold value. In such an example, the assessment may be compared against a predetermined threshold skill level and, if the assessed surgical skill did not meet the threshold, a notification may be generated. The notification may include different information according to different examples. For example, the notification may be generated for the surgeon that performed the particular surgical technique and may indicate that their technique was of poor quality or that one or more training exercises were recommended to improve upon the skill. In some examples, the notification may be generated for a supervising surgeon, e.g., an attending surgeon, a department head, a medical school professor, etc., indicating the assessment and recommending training for the surgeon. In examples where the same surgeon has demonstrated low skill with multiple different techniques, the system may output a notification to a supervising surgeon or a medical center administrator that the surgeon has a low skill level.

In some examples, the notification may be generated based on an assessment of a surgical skill exceeding a threshold indicating a very high level of skill. For example, the system may assess skill according to multiple different predetermined thresholds, e.g., poor quality, acceptable quality, good quality, exceptional quality, etc. If the assessment satisfies the threshold for "exceptional quality," the notification may indicate to the surgeon that their technique was exceptional or the notification may be provided to a supervising surgeon indicating the high quality of the technique. In some examples, the portion of the input data, e.g., a surgical video, may be highlighted on a surgical web portal available to one or more surgeons within a medical center or medical school as a high-quality example of the corresponding surgical technique or it may be recommended to one or more surgeons as a training example for the surgical technique.

In some examples where the method 600 is performed in real-time during a surgery, notifications may be generated and output during the surgery. For example, if an error is detected by the surgery analysis software 402, the surgery analysis software 402 may generate a notification and provide the notification to a screen assigned to a supervising surgeon in the OR indicating an error. In some examples, the notification may include the portion of the input data corresponding to the event to allow the supervising surgeon to view the potential error and determine any corrective action. Further, if the system detects that the surgeon is making unrecognized movements or is using poor technique, it may output a notification that the surgeon may be about to commit an error. Alternatively, if the system 400 detects that the surgeon has performed a surgical technique with a high degree of skill, a notification may be generated and provided to the supervising surgeon to provide positive feedback during or after the surgery. Further, if, during a surgery, an abnormal anatomy is recognized, the system 400 may identify one or more videos having similar abnormal anatomy tagged in them and present one or more to the surgeon with an option to view them.

It should be appreciated that the discussion of the example method 600 illustrated a particular example or examples and the disclosure is not limited to such examples. Further, it should be appreciated that certain aspects of the method 600 may be omitted or re-ordered in some examples. For example, one or more of blocks 650-670 may be omitted in some examples. Further, in some examples, the first and second ML models may be the same model, such as discussed above with respect to FIG. 5.

Figure 7:
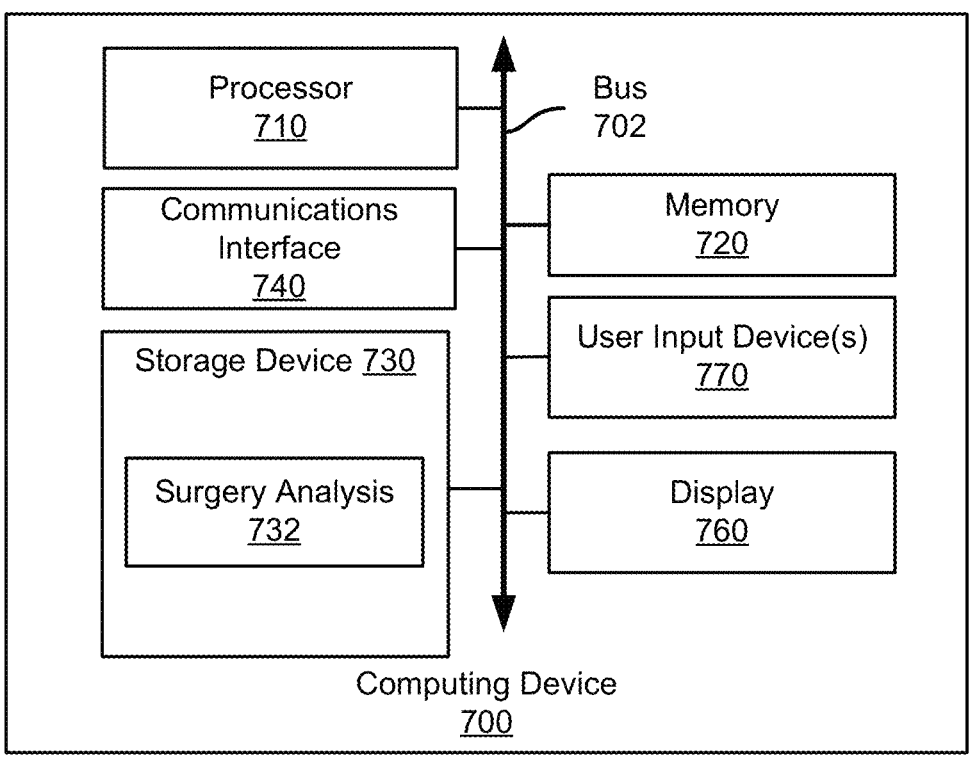
FIG. 7 shows an example computing device suitable for use with systems and methods for detecting events during a surgery.

Referring now to FIG. 7, FIG. 7 shows an example computing device 700 suitable for use in example systems or methods for detecting events during a surgery according to this disclosure. The example computing device 700 includes a processor 710 which is in communication with the memory 720 and other components of the computing device 700 using one or more communications buses 702. The processor 710 is configured to execute processor-executable instructions stored in the memory 720 to perform one or more methods for detecting events during a surgery according to different examples, such as part or all of the example method 600 described above with respect to FIG. 6. The computing device, in this example, also includes one or more user input devices 750, such as a keyboard, mouse, touchscreen, microphone, etc., to accept user input. The computing device 700 also includes a display 740 to provide visual output to a user.

In addition, the computing device 700 includes a storage device 730, which comprises a non-volatile computer-readable medium that stores surgery analysis software 734, such as described above with respect to FIG. 4 or 5, that can be used to perform one or more methods according to this disclosure, such as the methods discussed above with respect to FIG. 7.

The computing device 700 also includes a communications interface 740. In some examples, the communications interface 730 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
receiving surgical video of a surgery comprising a plurality of video frames;
receiving data from a robotic surgical system corresponding to the surgery, wherein the data from the robotic surgical system comprises kinematic data corresponding to one or more arms of the robotic surgical system;
identifying, by a first trained machine-learning ("ML") model, an event during a surgical procedure based on the surgical video and the data from the robotic surgical system;
determining, by the first trained ML model, a subset of the plurality of video frames, the subset of the plurality of video frames corresponding to the event;
determining, by a second trained ML model, a characteristic of the event based on the subset of the plurality of video frames and the data from the robotic surgical system;
generating metadata corresponding to event based on the characteristic of the event;
extracting and storing a video clip comprising the subset of the plurality of video frames from the plurality of video frames; and
extracting and storing robotic log data corresponding to the event.

2. The method of claim 1, further comprising:
identifying, by the first trained ML model, a plurality of events during the surgical procedure based on the surgical video;
determining, for each event of the plurality of events by the first trained ML model, a respective subset of the plurality of video frames corresponding to the event;
determining, for each event by the second trained ML model, a respective characteristic of the respective event; and
generating, for each event, metadata corresponding to the respective event based on the respective characteristic of the respective event.

3. The method of claim 1, wherein the data from the robotic surgical system comprises audio data.

4. The method of claim 1, wherein the event comprises a surgical technique, and wherein the characteristic comprises an assessment of surgical skill.

5. The method of claim 4, further comprising:
comparing the assessment to a threshold level of surgical skill; and
responsive to the assessment exceeding the threshold level of surgical skill, including in the metadata an indicator of a training example for the surgical skill.

6. The method of claim 5, further comprising notifying one or more surgeons of the surgical video and indicating it as a training example for the surgical skill.

7. The method of claim 4, further comprising:
comparing the assessment to a threshold level of surgical skill; and
responsive to the assessment not meeting the threshold level of surgical skill, generating metadata indicating further training to be provided to a surgeon performing the surgical skill in the video.

8. The method of claim 7, further comprising outputting a notification indicating that the surgeon may be about to commit an error.

9. The method of claim 7, further comprising outputting a notification suggesting one or more training examples for the surgical skill.

10. The method of claim 7, further comprising:

identifying the surgeon as having low skill for the surgical skill;

determining the surgeon has low skill for multiple surgical skill; and outputting a notification indicating the surgeon is a low-skill surgeon.

11. The method of claim 1, further comprising:

detecting an error, by the second trained ML model, during the surgery; and outputting a notification indicating the error.

12. The method of claim 1, wherein the event comprises an adverse event.

13. The method of claim 12, further comprising outputting a notification to one or more members of a surgical team indicating the adverse event.

14. A system comprising:

a non-transitory computer-readable medium; and a processor communicatively coupled to the non-transitory computer-readable medium and configured to execute processor executable instructions stored in the non-transitory computer-readable medium to:

receive surgical video of a surgery comprising a plurality of video frames;

receive data from a robotic surgical system corresponding to the surgery, wherein the data from the robotic surgical system comprises kinematic data corresponding to one or more arms of the robotic surgical system;

identify, using a first trained machine-learning ("ML") model, an event during a surgical procedure based on the surgical video and the data from the robotic surgical system;

determine, using the first trained ML model, a subset of the plurality of video frames, the subset of the plurality of video frames corresponding to the event;

determine, using a second trained ML model, a characteristic of the event based on the subset of the plurality of video frames and the data from the robotic surgical system;

generate metadata corresponding to event based on the characteristic of the event;

extract and store a video clip comprising the subset of the plurality of video frames from the plurality of video frames; and extract and store robotic log data corresponding to the event.

15. The system of claim 14, further comprising:

identifying, by the first trained ML model, a plurality of events during the surgical procedure based on the surgical video;

determining, for each event of the plurality of events by the first trained ML model, a respective subset of the plurality of video frames corresponding to the event;

determining, for each event by the second trained ML model, a respective characteristic of the respective event; and generating, for each event, metadata corresponding to the respective event based on the respective characteristic of the respective event.

16. The system of claim 14, wherein the data from the robotic surgical system comprises audio data.

17. The system of claim 14, wherein the event comprises a surgical technique, and wherein the characteristic comprises an assessment of surgical skill.

18. The system of claim 17, further comprising:

comparing the assessment to a threshold level of surgical skill; and responsive to the assessment exceeding the threshold level of surgical skill, including in the metadata an indicator of a training example for the surgical skill.

19. The system of claim 17, further comprising:

comparing the assessment to a threshold level of surgical skill; and responsive to the assessment not meeting the threshold level of surgical skill generating metadata indicating further training to be provided to a surgeon performing the surgical skill in the video.

20. The system of claim 14, further comprising:

detecting an error, by the second trained ML model, during the surgery; and outputting a notification during the surgery indicating the error.

21. The system of claim 14, wherein the event comprises a surgical technique, wherein the surgical technique is a non-standard technique.

22. The system of claim 14, wherein the event comprises an abnormal anatomical feature.

23. The system of claim 14, wherein the event comprises an adverse event.

24. A non-transitory computer-readable medium comprising processor executable instructions stored in the non-transitory computer-readable medium to:

receive surgical video of a surgery comprising a plurality of video frames;

receive data from a robotic surgical system corresponding to the surgery, wherein the data from the robotic surgical system comprises kinematic data corresponding to one or more arms of the robotic surgical system;

identify, using a first trained machine-learning ("ML") model, an event during a surgical procedure based on the surgical video and the data from the robotic surgical system;

determine, using the first trained ML model, a subset of the plurality of video frames, the subset of the plurality of video frames corresponding to the event;

determine, using a second trained ML model, a characteristic of the event based on the subset of the plurality of video frames and the data from the robotic surgical system;

generate metadata corresponding to event based on the characteristic of the event;

extract and store a video clip comprising the subset of the plurality of video frames from the plurality of video frames; and extract and store robotic log data corresponding to the event.

\* \* \* \* \*